US008853075B2

(12) United States Patent
Gatineau et al.

(10) Patent No.: US 8,853,075 B2
(45) Date of Patent: Oct. 7, 2014

(54) METHOD FOR FORMING A TITANIUM-CONTAINING LAYER ON A SUBSTRATE USING AN ATOMIC LAYER DEPOSITION (ALD) PROCESS

(75) Inventors: Satoko Gatineau, Ibaraki (JP); Christian Dussarrat, Wilmington, DE (US); Christophe Lachaud, Saint Michel sur Orge (FR); Nicolas Blasco, Grenoble (FR); Audrey Pinchart, Antony (FR); Ziyun Wang, Newark, DE (US); Jean-Marc Girard, Paris (FR); Andreas Zauner, Voisons le Bretonneux (FR)

(73) Assignee: L'Air Liquide Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 426 days.

(21) Appl. No.: 12/920,026

(22) PCT Filed: Feb. 13, 2009

(86) PCT No.: PCT/EP2009/051683
§ 371 (c)(1),
(2), (4) Date: Jul. 26, 2011

(87) PCT Pub. No.: WO2009/106433
PCT Pub. Date: Sep. 3, 2009

(65) Prior Publication Data
US 2011/0275215 A1 Nov. 10, 2011

(30) Foreign Application Priority Data
Feb. 27, 2008 (EP) .................................. 08305035

(51) Int. Cl.
H01L 21/4763 (2006.01)
H01J 31/12 (2006.01)
H01J 29/86 (2006.01)

(52) U.S. Cl.
CPC ............... *H01J 29/86* (2013.01); *H01J 31/127* (2013.01); *H01J 2201/30469* (2013.01)
USPC .................... 438/648; 438/656; 257/E21.295

(58) Field of Classification Search
USPC ........... 438/681, 685, 648, 765; 257/E21.295
See application file for complete search history.

(56) References Cited

U.S. PATENT DOCUMENTS 5,846,895 A 12/1998 Gila et al.
5,861,352 A 1/1999 Gila et al.
(Continued)

FOREIGN PATENT DOCUMENTS

EP 0 808 841 11/1997
EP 1 067 595 1/2001
(Continued)

OTHER PUBLICATIONS

Carta, G. et al., "Thermal properties of volatile organohafnium precursors for $HfO_2$ MOCVD processes," Electrochem Soc Proceedings, 260, Sep. 2005.
(Continued)

*Primary Examiner* — W. Wendy Kuo
*Assistant Examiner* — Shaka White
(74) *Attorney, Agent, or Firm* — Patricia E. McQueeney

(57) ABSTRACT

Methods of forming titanium-containing layers on substrates are disclosed. In the disclosed methods, the vapor of a precursor compound having the formula $Ti(Me_5Cp)(OR)_3$, wherein R is selected from methyl, ethyl, or isopropyl is provided. The vapor is reacted with the substrate according to an atomic layer deposition process to form a titanium-containing complex on the surface of the substrate.

20 Claims, 1 Drawing Sheet $(Me_5Cp)Ti(OMe)_3$

(56) References Cited

U.S. PATENT DOCUMENTS

| | | | |
|---|---|---|---|
| 6,001,742 | A | 12/1999 | Chang |
| 6,197,683 | B1 | 3/2001 | Kang et al. |
| 6,268,448 | B1 | 7/2001 | Collins et al. |
| 6,445,023 | B1 | 9/2002 | Vaartstra et al. |
| 6,669,990 | B2 | 12/2003 | Min et al. |
| 6,689,675 | B1 | 2/2004 | Parker et al. |
| 6,743,473 | B1 | 6/2004 | Parkhe et al. |
| 6,984,591 | B1 | 1/2006 | Buchanan et al. |
| 7,108,747 | B1 | 9/2006 | Leskala et al. |
| 2002/0042165 | A1 | 4/2002 | Putkonen |
| 2002/0106451 | A1 | 8/2002 | Skarp et al. |
| 2004/0235312 | A1 | 11/2004 | Loftin et al. |
| 2005/0112874 | A1* | 5/2005 | Skarp et al. ............ 438/680 |
| 2005/0260357 | A1 | 11/2005 | Olsen et al. |
| 2006/0062910 | A1 | 3/2006 | Meiere |
| 2006/0097305 | A1 | 5/2006 | Lee |
| 2006/0228888 | A1 | 10/2006 | Lee et al. |
| 2006/0269667 | A1 | 11/2006 | Ma et al. |
| 2008/0081113 | A1* | 4/2008 | Clark ............ 427/255.394 |
| 2008/0102205 | A1 | 5/2008 | Barry et al. |
| 2008/0308793 | A1* | 12/2008 | Jeong et al. ............ 257/40 |
| 2009/0074983 | A1* | 3/2009 | Heys et al. ............ 427/569 |
| 2009/0203222 | A1 | 8/2009 | Dussarrat et al. |
| 2009/0215225 | A1 | 8/2009 | Stender et al. |
| 2009/0233439 | A1 | 9/2009 | Park et al. |
| 2009/0311879 | A1 | 12/2009 | Blasco et al. |

FOREIGN PATENT DOCUMENTS

| | | |
|---|---|---|
| EP | 1 524 299 | 4/2005 |
| JP | 32 30805 | 11/1999 |
| JP | 2001 102326 | 4/2001 |
| JP | 2001 355070 | 12/2001 |
| JP | 2002 060944 | 2/2002 |
| JP | 2002 069641 | 3/2002 |
| JP | 2002 093803 | 3/2002 |
| JP | 2002 525426 | 8/2002 |
| JP | 2004 507551 | 3/2004 |
| JP | 2004 300579 | 10/2004 |
| JP | 2004 349710 | 12/2004 |
| JP | 2005 504432 | 2/2005 |
| JP | 2005 104994 | 4/2005 |
| JP | 2005 171291 | 6/2005 |
| JP | 2005 209766 | 8/2005 |
| JP | 2005 536064 | 11/2005 |
| JP | 2005 351450 | 12/2005 |
| JP | 2006 165537 | 6/2006 |
| KR | 2007 012181 | 12/2007 |
| KR | 2008 0101040 | 11/2008 |
| WO | WO 02 18394 | 3/2002 |
| WO | WO 02 90614 | 11/2002 |
| WO | WO 2004 010469 | 1/2004 |
| WO | WO 2005 113852 | 12/2005 |
| WO | WO 2005 124849 | 12/2005 |
| WO | WO 2006 131751 | 12/2006 |
| WO | WO 2007 005088 | 1/2007 |
| WO | WO 2007 011973 | 1/2007 |
| WO | WO 2007 030673 | 3/2007 |
| WO | WO 2007 140813 | 12/2007 |
| WO | WO 2008 137239 | 11/2008 |
| WO | WO 2009 036045 | 3/2009 |
| WO | WO 2009 036046 | 3/2009 |
| WO | WO 2009 106433 | 9/2009 |
| WO | WO 2007 141059 | 12/2009 |

OTHER PUBLICATIONS

Caymax, M. et al., "High-k materials for advanced gate stack dielectrics: a comparison of ALCVD and MOCVD as deposition technologies," Mat. Res. Soc. Symp. Proc. vol. 765, 2003.

Chandra, G. et al. "Amido-derivatives of metals and metalloids. Part VI. Reactions of titanium(IV), zirconium(IV), and hafnium(IV) amides with protic compounds." Journal of Chemical Society (A), 1968, pp. 1940-1945.

Chang, H.S. et al. "Electrical and physical properties of $HfO_2$ deposited via ALD using $Hf(OtBu)_4$ and ozone atop $Al_2O_3$." Electrochem. Solid-State Letters, 7 (6) F42-F44 (2004).

Codato, S., et al. "MOCVD growth and characterization of $ZrO_2$ thin films obtained from unusual organo-zirconium precursors." Chemical Vapor Deposition, Wiley-VCH Verlag, Weinheim, Germany, vol. 11, No. 11, 1999, pp. 159-164.

Hausmann, D.M. et al. "Atomic layer deposition of hafnium and zirconium oxide using metal amide precursors." Chem., Mater. 2002, 14, 4350-4353.

Juppo, M. et al. "In situ mass spectrometry study on surface reactions in atomic layer deposition of $Al_2O_3$ thin films from trimethylaluminum and water." Langmuir 2000, 16, pp. 4034-4039.

Kawahara, T. et al. "Effect of Hf source, oxidizing agents, and $NH_3$/Ar plasma on the properties of $HfAlO_x$ films prepared by atomic layer deposition." J. Appl. Phys., vol. 43, No. 7A, 2004, pp. 4129-4134.

Kukli, K. et al., "Atomic layer deposition of hafnium dioxide films from 1-methoxy-2-methyl-2-propanolate complex of hafnium," Chem. Mater. 2003, 15, pp. 1722-1727.

Lehn, J.-S. et al., "New precursors for the CVD of zirconium and hafnium oxide films," Chemical Vapor Deposition 2006, 12, No. 5, pp. 280-284.

Niinisto, J. et al. "In situ quadrupole mass spectrometry study of atomic-layer deposition of $ZrO_2$ using $Cp_2Zr(CH_3)_2$ and water." Langmuir, 7321, 21, 2005.

Potter, R.J. et al., "Deposition of $HfO_2$, $Gd_2O_3$ and $PrO_x$ by liquid injection ALD techniques," Chemical Vapor Deposition 2005, 11, No. 3, pp. 159-169.

Putkonen, M. et al. "Zirconia thin films by atomic layer epitaxy. A comparative study on the use of novel precursors with ozone." J. Mater. Chem., 3141, 11, 2001.

Senzaki, Y. et al. "Atomic layer deposition of hafnium oxide and hafnium silicate thin films using liquid precursors and ozone," J. Vac. Sci. Technol. A 22(4), Jul./Aug. 2004.

Triyoso, D.H. et al. "Physical and electrical characteristics of $HfO_2$ gate dielectrics deposited by ALD and MOCVD." J. Electrochem. Soc., 152 (3) G203-G209 (2005).

International Search Report and Written Opinion for co-pending PCT/EP2009/051683, May 14, 2009.

International Search Report and Written Opinion for related PCT/EP2006/062893, Sep. 27, 2007.

International Search Report and Written Opinion for related PCT/EP2006/052507, Oct. 31, 2007.

Cotton, S.A., "Ti, Zr, and Hf," Annu. Repo. Prog. Chem., Sect. A: Inorg. Chem., 1993, 90, p. 119-130.

Kim, M-S et al., "ALD analyses of HfCl4 + O3 and HfCl4 + H2O by mass spectroscopy," Electrochemical Society Proceedings vol. 2005-05, pp. 397-403.

Williams, P.A. et al., "Novel mononuclear alkoxide precursors for the MOCVD of ZrO2 and HfO2 thin films," Chem Vap. Deposition 2002, 8, No. 4, pp. 163-170.

Handbook of Thin Film Materials, Had Singh Nalwa, ed., Academic Press, New York, 2002, pp. 103-159.

Becker, J.S. et al., "Atomic Layer Deposition of Hafnium and Zirconium Nitrides", Chem. Mater. 2004, 16, 3497-3501.

Cano, J. et al., "Neutral and Cationic [Bis(n1-amidosilyl)-n5-cyclopentadienyl]titanium and -zirconium Complexes: Synthesis, X-ray Molecular Structures and DFT Calculations", Eur. J. Inorg. Chem. 2003 2463-2474.

Chen, P. et al., "Effect of nitrogen containing plasmas on interface stability of hafnium oxide ultrathin films on Si(100)," Applied Physics Letters, Aug. 30, 2004, vol. 85, No. 9, pp. 1574-1576.

Ciruelo, G. et al., "Synthesis and reactivity of new silyl substituted monocyclopentadienyl zirconium complexes. X-ray molecular structure of $[Zr(N^5-C_5H_4(SiMe_2CH_2Ph))(CH_2Ph)_3]$", Journal of Organometallic Chemistry 547 (1997) 287-296.

Herrmann, W.A. et al., "Volatile metal alkoxides according to the concept of donor functionalization," Angewandte Chemie International Edition in English, (1995) vol. 34, pp. 2187-2206.

Irigoyen, a.M. et al., Synthesis and Characterization of chlorobis(dialkylamido) and alkylbis(dialkylamido) derivatives of $[(n^5-C_5Me_5)MCl_3]$(M=Ti, Zr), Journal of Organometallic Chemistry, 494 (1995) 255-259.

(56) References Cited

OTHER PUBLICATIONS

Jutzi, P. et al., "Halbsandwich-Komplexe der Elemente Titan and Zirconium mit dem (Diisopropylaminoethyl) cyclopentadienyl-Ligand: Molekülstruktur von [($C_5H_4CH_2CH_2N(H)^iPr_2$)$ZrCl_3$]$^+Cl^-$•$2CH_3OH$", Journal of Organometallic Chemistry 533 (1997), 237-245.

Kukli, K. et al., "Influence of growth temperature on properties of zirconium dioxide films grown by atomic layer deposition," Journal of Applied Physics, Aug. 15, 2002, vol. 92, No. 4, p. 1833-1840.

Niinisto, J. et al., "Development of Novel Processes for Atomic Layer Deposition of High-k Dielectrics", $72^{nd}$ Annual Meeting of the DPG, Feb. 27, 2008, Berlin.

Pinchart, A. et al., "Novel Thermally-Stable Hafnium and Zirconium ALD Precursors", IEEE/SEMI Advanced Semiconductor Manufacturing Conference (ASMC) 2007.

Putkonen, M. et al., "Organometallic precursors for atomic layer deposition," Topics in Organometallic Chemistry (2005) pp. 125-145.

Rie, K.-T. et al., "Plasma assisted CVD for low temperature coatings to improve the wear and corrosion resistance," Surface and Coatings Technology (1996) vol. 86-87, pp. 498-506.

Rogers, J.S. et al., "Fulvene to Cyclopentadienyl Conversion with Homoleptic Complexes of Zirconium and Hafnium", Organometallics 1999 18, 3976-3980.

Schneider, H. et al., "Immobilization of n5-cyclopentadienyltris(dimethylamido) zirconium polymerization catalysts on a chlorosilane- and HMDS-modified mesoporous silica surface: a new concept for supporting metallocene amides towards heterogenous single-site-catalysts", Journal of Molecular Catalysis A: Chemical 170 (2001) 127-141.

Vollmerhaus, R. et al., "Synthesis and structure of Group 4 iminophosphonamide complexes," Organometallics, 2005, vol. 24, pp. 494-507.

Winter, C.H. et al., "Metallic Materials Deposition: Metal-organic Precursors," Encyclopedia of Inorganic Chemistry, 2006, John Wiley & Sons Ltd., DOI: 10.1002/ 0470862106.ia138.

\* cited by examiner

METHOD FOR FORMING A TITANIUM-CONTAINING LAYER ON A SUBSTRATE USING AN ATOMIC LAYER DEPOSITION (ALD) PROCESS

This application is a 371 of International PCT Application PCT/EP2009/051683, filed Feb. 13, 2009, which claims priority to European Patent Application No. 08305035.1 filed Feb. 27, 2008, the entire contents of which are incorporated herein by reference.

The invention relates to a method for forming a titanium-containing layer on a substrate using an ALD (Atomic Layer Deposition) process.

The new requirements in terms of dimensions for the future generation semiconductor devices, lead to the development of new materials with a high dielectric constant. High-k dielectrics materials are required in CMOS device to replace $SiO_2$ which reaches its physical limits with a typical thickness of 1 nm. Similarly, high-k dielectrics are required in Metal-Insulator-Metal architectures for DRAM applications. Various metal compositions have been considered to fulfil both the materials requirements (k, leakage current, crystallization temperature, charge trapping) and the integration requirements (for example, thermal stability on interface or dry etching feasibility). Titanium based oxides are among the most promising candidates, as for instance a Ti containing mixed oxide film, $TiO_2$, $SrTiO_3$, $(Ba,Sr)TiO_3$, $Pb(Ti)O_3$, $Ti(OiPr)_4$, $TiLnO_x$ (Ln being selected among lanthanide and rare-earth elements) and more generally $TiMOx$, M being an element selected from group II, group IIIa and IIIb, or a transition metal.

Furthermore, hafnium, zirconium and titanium metals composition can also be considered for electrode and/or Cu diffusion barrier applications, such as TiN, HfN, ZrN, HfSi, ZrSi, HfSiN, ZrSiN for MIM electrodes.

Vapor phase deposition is the main industrial way to depose thin films with reasonable throughput and acceptable purity. Those techniques could be MOCVD (Metal-organic Chemical Vapor Deposition) or ALD (Atomic Layer Deposition). Metal-organic or metal-halide precursors are required for those processes. Various hafnium, zirconium and titanium metal-organic compounds have been considered as precursors to enable such deposition.

Halides such as $HfCl_4$, $ZrCl_4$ are commonly used as Hf or Zr precursors and have been widely described. Triyoso et al. [Journal of Applied Physics 97 (2005) 124107], Kawahara et al. [Japanese Journal of Applied Physics 43 (2004) 4129], Caymax et al. [Material Research Society symp proc Vol 765 (2003) 47], evaluated $HfCl_4$ for the deposition of $HfO_2$ by ALD. The main disadvantage is the generation during the deposition process of some by-products such as HCl or $Cl_2$. Those compounds can cause surface/interface roughness that can be detrimental to the final properties. Other possible by-products, depending on the O-source, might be hazardous. Moreover, in the case of high-k oxide, Cl or F impurities are highly detrimental to the final electrical properties.

Alkoxides, such as $Hf(OtBu)_4$, $Zr(OtBu)_4$, $Hf(OtBu)_2$ $(mmp)_2$ and $Hf(mmp)_4$, (mmp=1-methoxy-2-methyl-2-propanolate), have been evaluated, for instance by Kukli et al. [Chem. Mater. 15 (2003) 1722], and Potter et al. [Chem. Vap. Dep. 11 (2005) 159]. However, as suggested by Potter et al., factors like β-hydride elimination of the alkoxide ligand may prevent the ALD self-limitation. A direct comparison between $Hf(OtBu)_4$ and $Hf(NEtMe)_4$ (Senzaki et al. [J. Vac. Sc. Techn. A 22 (2004) 1175]) showed much lower impurity (C, H) content in the oxide film for the latter precursor.

Alkylamides precursors $(Hf(EMA)_4, Hf(DMA)_4, Hf(DEA)_4)$ have been widely studied. The deposition of $HfO_2$ from TEMAH by ALD was studied by Senzaki et al [J. Vac. Sc. Techn. A 22 (2004) 1175] Kawahara et al. [JJAP 43 (2004) 4129] and others. Those alkylamides are both suitable for ALD and MOCVD processes and present interesting properties for distribution since they are liquid at room temperature (TDEAH and TEMAH) and of sufficient volatility. Furthermore, they allow self-limited ALD at low temperature for limited thermal budget processes. The drawback of the Group IV alkylamide precursors is their limited thermal stability and in particular zirconium compounds and so, they may decompose slightly during the distribution, can generate particles during deposition, may entail un-uniform composition during deep trenches deposition processes and they do not allow a large self-limited ALD temperature window, hence reducing the process window. In particular, $Zr(NEtMe)_4$ may decompose in the distribution lines and generate particles above 170° C. which is a common distribution temperature. $Hf(NEtMe)_4$ is more thermally stable yet do not afford self-limited atomic layer deposition above 300° C. due to thermal decomposition.

In WO2007/005088, Thenappan et al. disclose hafnium and zirconium guanidinates complexes and their application for vapor phase deposition. $Hf(NEt_2)_2((NiPr—CNEt_2)_2$ is given as example. Hafnium and zirconium guanidinates are however generally solids with very limited volatility. As exemplified in WO2007/005088, thermal gravimetric analysis, one may not obtain $Hf(NEt_2)_2((NiPr—CNEt_2)_2$ in vapour phase without risk of thermal decomposition and subsequent particle generation.

Lehn et al. [CVD 12 (2006) 280] have introduced new tetrakis(trimethylhydrazido)zirconium and hafnium $Zr(NMeNMe_2)_4$ and their use for low temperature CVD. The exemplified compounds have acceptable volatility (sublimation at 0.06 Torr, 90° C. reported) but present the disadvantage of being solid at room temperature.

Carta et al. (Electrochem Soc Proceedings, 260, 2005-09, 2005) have introduced a new family of Zr and Hf compounds as alternative to hafnium and zirconium alkylamides: Bis(cyclopentadienyl)bisdimethyl hafnium, biscyclopentadienylbisdimethylzirconum. They allow efficient ALD with an ALD window up to 400° C. and achievement of film with less than 0.2% C in optimized conditions with $H_2O$ as co-reactant. However, $HfCp_2Me_2$ and $ZrCp_2Me_2$ are both solid at room temperature. $HfCp_2Me_2$ melting point is 57.5° C. This prevents IC makers to use those precursors in an industrial manner, that is using delocalized containers filling, and entail both facilitation and process issues. Liquid dicyclopentadienyl derivatives have recently been proposed by Heys et al. in WO2006/131751 A1. However, they still present the disadvantage of limited volatility and also present large steric hindrance that may limit the achieved growth rate.

Heys et al. in WO2006/131751A1 have introduced the bis(cyclopentadienyl)bis(alkoxyde) hafnium and zirconium family. However, $HfCp_2(OMe)_2$ and $HfCp_2(OMe)_2$ has the major drawback of being solid. They present the disadvantage to be thermally unstable. A thermogravimetric analysis shows 20% of residues for an end of vaporization at 310° C. The second drawback for a using in an industrial manner is their solid state.

The main industrial options to enable the deposition of highly uniform and conformal thin films with reasonable throughput in high aspect ratio structures are techniques such as MOCVD (Metal-Organic Chemical Vapor Deposition) or ALD (Atomic Layer Deposition).

However, films deposited by MOCVD need high thermal budget and generally follow a 3D-growth mechanism described by a Volmer-Weber model. Thin films grow by clusters nucleation and such technique also leads to insufficient step coverage.

The typical ALD process (e.g as described in RITALA M., LESKELA M., Atomic Layer Deposition, Handbook of thin films materials) involves gaseous reactants led onto a substrate by pulses, separated by inert gas purging. In MOCVD, gaseous reactants are injected simultaneously and react by thermal self-decomposition while in ALD; the loss of the ligand is thermally induced by reaction with the surface groups on the substrate. In a temperature range, the surface reactions are self-limited, which allow the deposition of highly uniform and conformal films. Precursors must be volatile and stable enough to be easily transferred to the reaction chamber without being decomposed. Moreover, they must be reactive enough with the chemical groups of the surface to ensure reasonable growth rate.

However, common group IV or V (Ti, V, Nb, Ta) based metal-organic precursors are not suitable for the deposition without assisting the thermal ALD process by plasma techniques.

According to the present invention, surprisingly, it appears that in applying Atomic Layer Deposition techniques to a molecule which could have been first proposed for Chemical Vapor Deposition, allows to get very good $TiO_2$ films and solves the inconvenients cited above.

Moreover, using such metal-organic precursors by MOCVD at 600° C., can not be suitable for the deposition of highly uniform, conformal thin films. Such deposition will result in an excessive carbon contamination and poor step coverage in high aspect ratio structures.

Nevertheless, according to the state of the art, MOCVD process is the best solution in terms of interesting growth rate, so others processes have never been implemented.

SUMMARY

According to a first embodiment, the invention relates to a method for forming a titanium-containing layer on a substrate, the method comprising at least the steps of:

a) providing a vapor comprising at least one precursor compound of the formula $Ti(Me_5Cp)(OR)_3$ (I), wherein Me=methyl, Cp=cyclopentadienyl, and R is selected in the group consisting in methyl, ethyl, isopropyl; or of the formula $Ti(R^1Cp)(OR^2)_3$ (II), wherein $R^1$ is selected from the group consisting in H, methyl, ethyl, isopropyl and $R^2$ is independently selected from the group consisting in methyl, ethyl, isopropyl or tert-butyl;

b) reacting the vapor comprising the at least one compound of formula (I) or (II) with the substrate, according to an atomic layer deposition process, to form a layer of a tantalum-containing complex on at least one surface of said substrate.

Furthermore, other embodiments of the invention are:
The method according to the invention further comprising the step:

c) reaction of the complex formed obtained in step b) with a reagent selected from another metal source, reducing reactants and/or nitriding reactants and/or oxidizing reactants.

The method wherein the vapour provided in step a) further comprises one or more metal (M')-organic precursor(s) to produce thin films containing titanium and M'. M' being independently selected from any other element in the group II, III-A, III-B, Sulpher (S), transition metal, lanthanoids, or rare-earth metals.

The method, further comprising providing at least one reaction gas wherein the at least one reaction gas is selected from the group consisting of hydrogen, hydrogen sulfide, hydrogen selenide, hydrogen telluride, carbon monoxide, ammonia, organic amine, silane, disilane, higher silanes, silylamines, diborane, hydrazine, methylhydrazine, chlorosilane and chloropolysilane, metal alkyl, arsine, phosphine, trialkylboron, oxygen, ozone, water, hydrogen peroxide, nitrous oxide, nitrogen monoxide, nitrogen dioxide, alcohols, plasma comprising fragments of those species, and combinations thereof, preferably ozone or water.

The method, wherein the titanium precursor of formula (I) or (II) is selected in the group consisting of:
$Ti(MeCp)(OEt)_3$; $Ti(MeCp)(OiPr)_3$; $Ti(MeCp)(OtBu)_3$; $Ti(EtCp)(OEt)_3$; $Ti(EtCp)(OiPr)_3$; $Ti(EtCp)(OtBu)_3$; $Ti(Cp)(OEt)_3$; $Ti(Cp)(OiPr)_3$; $Ti(Cp)(OtBu)_3$; $Ti(Me_5Cp)(OMe)_3$; $Ti(MeCp)(OMe)_3$, $Ti(MeCp)(OEt)_3$, $Ti(MeCp)(OiPr)_3$, $Ti(MeCp)(OtBu)_3$, $Ti(EtCp)(OMe)_3$, $Ti(EtCp)(OEt)_3$, $Ti(EtCp)(OiPr)_3$, $Ti(EtCp)(OtBu)_3$, $Ti(Cp)(OMe)_3$, $Ti(Cp)(OEt)_3$, $Ti(Cp)(OiPr)_3$, $Ti(Cp)(OtBu)_3$; $Ti(iPrCp)(OMe)_3$, $Ti(iPrCp)(OEt)_3$, $Ti(iPrCp)(OiPr)_3$, $Ti(iPrCp)(OtBu)_3$, preferably $Ti(Me_5Cp)(OMe)_3$.

The method, wherein the temperature of the substrate is 25° C. to 600° C., preferably 380° C. to 425° C., and wherein the atomic layer deposition chamber containing the substrate has a pressure of 0.133 Pa to 133 kPa, preferably below 27 kPa.

The method, further comprising the step of purging excess vapor comprising the at least one compound of formula (I) from the substrate, with an inert gas selected from the group consisting of hydrogen, nitrogen, helium, argon, and mixtures thereof.

A method of manufacturing a semiconductor structure, comprising the steps of the method defined in the present invention, wherein the substrate is a semiconductor substrate.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
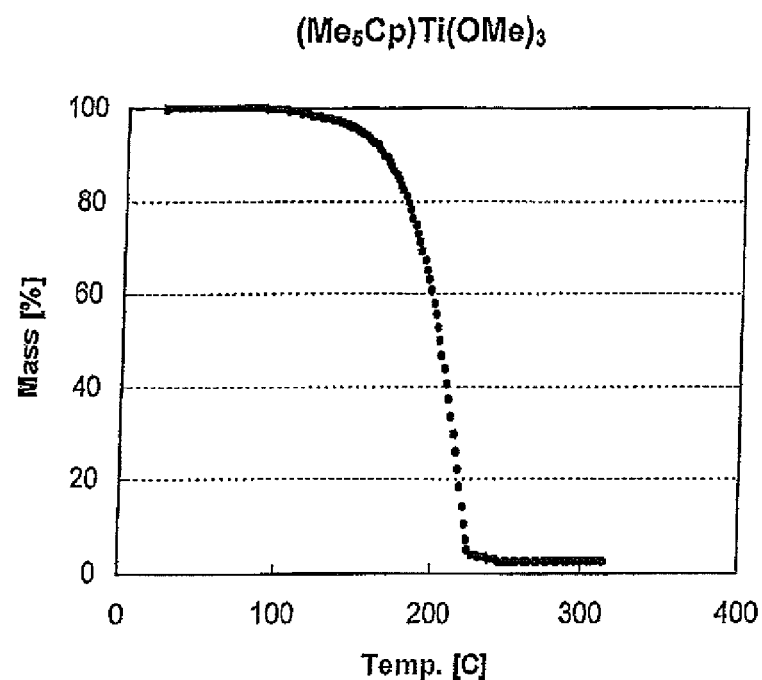
FIG. 1 is a graph of the percent residual mass of pentamethylcyclopentadienyl trimethoxy titanium, $Ti(Me_5Cp)(OMe)_3$, as a function of temperature during Thermo-Gravimetric Analysis (TGA)

The invention includes methods to achieve the desired results, as described, but is not limited to the various embodiments disclosed.

A New Technique to Deposit Titanium Containing Films Using Metal-Organic Precursors Described by the Following General Formula $Ti(Me_5Cp)(OR)_3$ as Material Source.

The vaporization of the titanium source is realized by introducing a carrier gas into a heated container containing the said metal source. The container is preferably heated at a temperature allowing to get the said metal source at a sufficient vapor pressure. The carrier gas can be selected from Ar, He, $H_2$, $N_2$ or mixtures of them. The said titanium source can be mixed to a solvent or to another metal source or to a mixture of them in the container. The container can for instance be heated at temperatures in the range of 25° C.-300° C., preferably below 150° C. Those skilled in the art will consider that the temperature of the container can be adjusted to control the amount of precursor vaporized. To control the evaporation level in the container, the pressure in the container can be modified. By reducing the pressure in the container, the level of vaporization of the titanium source can be increased. The pressure in the container can for instance be changed in the range of 0.133 Pa until 133 kPa, preferably below 27 kPa.

The said titanium source can also be fed in liquid state to a vaporizer where it is vaporized. The said metal source can be mixed to a solvent. The said titanium source can be mixed to another metal source. The said mixture of metal sources can be mixed to a solvent or a mixture of solvent. The said titanium source can be mixed to a stabilizer. The said solvent can be selected in the group consisting of alcanes such as hexane, heptane, octane, aromatic solvents such as benzene, toluene, mesitylene, xylene, silicon containing solvent such as hexamethyldisiloxane, hexamethyldisilazane, tetramethylsilane, sulphur containing solvents such as dimethylsulfoxide, oxygen containing solvent such as tetrahydrofuran, dioxane.

The said vaporized titanium source is then introduced into a reaction chamber where it is contacted to the surface of a substrate. The substrate can be heated to sufficient temperature to obtain the desired film at sufficient growth rate and with desired physical state and composition. Typical temperatures range from 150° C. to 600° C. Preferably the temperature is lower or equal to 450° C. The process can be assisted by a plasma technique. The use of plasma techniques allows to ionize the precursor vapor and/or the reactant used to form radicals and thus improve the reactivity of the said vaporized metal source and/or the reactivity of other gaseous species, used in the process.

The method of the present invention is a method assisted or not by plasma techniques, for depositing a titanium-containing film on the surface of a substrate comprising at least: exposition of the surface of a substrate to a titanium precursor described by the following general formula (I) or (II) and a reagent selected from reducing reactants, oxidizing reactants and/or nitriding reactants, to produce a titanium containing thin film on the surface. Example of reagent can be selected in the list: $H_2$, $N_2H_2$, methylhydrazine, $NH_3$, $SiH_4$, $Si_2H_6$, $Si_3H_8$, TSA, $Si_2Cl_6$ or any chrlorosilane or chloropolysilane, trimethylaluminium, $ZnEt_2$ or any metal alkyl, $BH_3$, $B_2H_6$, $PH_3$, $AsH_3$, trimethylboron, triethylboron, CO, monoamines, diamines, mixtures of them or plasma comprising fragment of those species. Example of oxidizing reagents can be selected in the list: $O_2$, $O_3$, $H_2O$, $H_2O_2$, NO, $NO_2$, $N_2O$, $CH_3OH$ or any alcohol, mixture of them or plasma comprising fragments of those species. Oxidizing species may alternatively be metal-organic compounds containing a metal-oxygen bond.

The deposition method, of this invention improves upon known methods by allowing the use of lower temperatures and producing higher quality films Furthermore, the thermal stability is improved: the ALD process will be provided with a higher temperature.

In one embodiment, the method of the invention consists in introducing alternatively a titanium-organic precursor described by the general formula (I) or (II) into a reaction chamber with a reagent. In a temperature range which depends on the precursor thermal stability and physical properties, the said titanium-organic precursor reacts in a self-limited manner with the chemical bonds present onto the surface of a substrate, chosen without limitation. Preferably, un-deposited titanium-organic precursors molecules are removed from the reaction chamber. The reagent introduced, reacts also in a self-limited manner.

Once all the complexes present on the surface of the substrate have reacted with the reagent, species are removed from the reaction chamber by a purge gas. The purge gas can for instance be selected within $N_2$, Ar, He, $H_2$ mixtures of them. The purge gas may additionally contain other gas species that do not modify the chemical reactivity of the surface. Alternatively, the purge can be realized by vacuum. This process can be repeated as many times as necessary to reach the desired film thickness. The reagent is selected from reducing reactants, nitriding reactants, oxidizing reactants, or a mixture of them. Example of reagent can be selected in the list: $H_2$, $N_2H_2$, methylhydrazine, $NH_3$, $SiH_4$, $Si_2H_6$, $Si_3H_8$, TSA, $Si_2Cl_6$ or any chrlorosilane or chloropolysilane, trimethylaluminium, $ZnEt_2$ or any metal alkyl, $BH_3$, $B_2H_6$, $PH_3$, $AsH_3$, trimethylboron, triethylboron, CO, monoamines, diamines, mixtures of them or plasma comprising fragment of those species. Example of oxidizing reagents can be selected in the list: $O_2$, $O_3$, $H_2O$, $H_2O_2$, NO, $NO_2$, $N_2O$, $CH_3OH$ or any alcohol, mixture of them or plasma comprising fragments of those species, preferably plasma comprising $H_2$, $NH_3$ or $O_2$. Oxidizing species may alternatively be metal-organic compounds containing a metal-oxygen bond.

In one embodiment, the method of the invention consists in introducing alternatively first a titanium-organic precursor described by the general formula (I) or (II) into a reaction chamber and second a reagent or another metal source. This another metal source being independently selected from any other element in the group II, III-A, III-B, Sulpher (S), transition metal, lanthanoids, or rare-earth metals. In a temperature range which depends on the precursor thermal stability and physical properties, the said metal-organic precursors react in a self-limited manner with the chemical bonds present onto the surface of a substrate. Preferably, un-deposited metal-organic precursors molecules are removed from the reaction chamber. The reagent introduced, reacts also in a self-limited manner.

In another embodiment of the invention, the said metal source is fed in liquid state to a vaporizer where it is vaporized. The said metal source can be mixed to another metal source. The said mixture of metal sources can be mixed to a solvent or a mixture of solvent. The said metal source can be mixed to a stabilizer. The said solvent can be selected for example from the group consisting of octane, hexane, pentane, tetramethylsilane.

The said vaporized metal source is introduced into a reaction chamber where it is contacted to a substrate. The substrate can be selected from the group consisting of Si, SiO2, SiN, SiON, W containing film and other metal containing films. The substrate can be heated to sufficient temperature to obtain the desired film at sufficient growth rate and with desired physical state and composition. Typical temperature ranges from 150° C. to 600° C. Preferably the temperature is lower or equal to 450° C. The pressure in the reaction chamber is controlled to obtain the desired metal containing film at sufficient growth rate. Typical pressure ranges from 1 m Torr ($133 \times 10^{-3}$ Pa) level to 100 Torr ($133 \times 10^2$ Pa) or higher.

In one embodiment of the invention, the said metal source is mixed to a reactant species prior to the reaction chamber.

In one embodiment of the invention where the targeted metal based film contains oxygen, such as for example metal oxide or metal oxy-nitride, the said reactant species include an oxygen source which is selected from, but not limited to, oxygen ($O_2$), oxygen radicals (for instance O or OH), for instance generated by a remote plasma, ozone ($O_3$), NO, $N_2O$, $NO_2$, moisture ($H_2O$) and $H_2O_2$.

In one embodiment of the invention where the targeted metal based film contains nitrogen, such as for example metal nitride or metal carbo-nitride, the said reactant species include a nitrogen source which is selected from, but not limited to nitrogen ($N_2$), ammonia, hydrazine and alkyl derivatives, N-containing radicals (for instance N, NH, $NH_2$), NO, $N_2O$, $NO_2$, amines.

In one embodiment of the invention where the targeted metal based film contains carbon, such as for example metal carbide or metal carbo-nitride, the said reactant species include a carbon source which is selected from, but not limited to, methane, ethane, propane, butane, ethylene, propylene, t-butylene, isobutylene, $CCl_4$.

In one embodiment of the invention where the targeted metal based film contains silicon, such as for example metal silicide, silico-nitride, silicate, silico-carbo-nitride, the said reactant species include a silicon source which is selected from, but not limited to, $SiH_4$, $Si_2H_6$, $Si_3H_8$, TriDMAS, BDMAS, BDEAS, TDEAS, TDMAS, TEMAS, $(SiH_3)_3N$, $(SiH_3)_2O$, trisilylamine, disiloxane, trisilylamine, disilane, trisilane, a alkoxysilane $SiH_x(OR^3)_{4-x}$, a silanol $Si(OH)_x(OR^3)_{4-x}$; preferably $Si(OH)(OR^3)_3$; more preferably $Si(OH)(OtBu)_3$, an aminosilane $SiH_x(NR^3R^4)_{4-x}$ (where x is comprised between 0 and 4; $R^3$ and $R^4$ are independently H or a C1-C6 carbon chain, either linear, branched or cyclic); preferably TriDMAS $SiH(NMe_2)_3$, BTBAS $SiH_2(NHtBu)_2$, BDEAS $SiH_2(NEt_2)_2$ and mixtures thereof. The targeted film can alternatively contain Germanium. The above-mentioned Si containing sources could be replaced by Ge containing sources.

The said first metal source, the possible said second metal source and the reactant species are introduced sequentially in the reaction chamber (atomic layer deposition). The reactor pressure is selected in the range from 1 mTorr ($133 \times 10^{-3}$ Pa) to 100 Torr ($133 \times 10^2$ Pa). Preferably, the reactor pressure is comprised between 1 and 10 Torr (1330 Pa). A purge gas is introduced between the metal source pulse and the reactant species pulse. The purge gas can be selected from the group consisting of $N_2$, Ar, He. The metal source, purge gas and reactant species pulse duration is comprised between 0.1 and 100 s. Preferably the pulse duration is comprised between 0.5 and 10 s.

In one embodiment of the invention, the second metal source is a lanthanide and rare-earth metal source (Sc, Y, La, Ce, Pr, Nd, Gd . . . ) source and is selected, but not limited to, from the group consisting of rare earth diketonates Ln(—O—$C(R^1)$—$C(R^2)$—$C(R^3)$—O—)(—O—$C(R^4)$—$C(R^5)$—$C(R^6)$—O—)(—O—$C(R^7)$—$C(R^8)$—$C(R^9)$—O—) (where each $R^i$ is independently H or a C1-C6 carbon chain, either linear, branched or cyclic), a cyclopentadienyl $Ln(R^1Cp)(R^2Cp)(R^3Cp)$ (where each $R^i$ is independently H or a C1-C6 carbon chain, either linear, branched or cyclic), $Ln(NR^1R^2)(NR^3R^4)(NR^5R^6)$ and mixtures thereof. The other metal source can alternatively be an aluminum source and is selected from, but not limited to, the group consisting of trimethylaluminum, dimethylaluminum hydride, an alkoxyalane $AlR^i_x(OR')_{3-x}$ (where x is comprised between 0 and 2; $R^1$ and $R^2$ are independently H or a C1-C6 carbon chain, either linear, branched or cyclic); preferably $AlR^1R^2OR'$, most preferably $AlMe_2(OiPr)$, an amidoalane $AlR^i_x(NR'R'')_{3-x}$ (where x is comprised between 0 and 2; $R^1$ and $R^2$ are independently H or a C1-C6 carbon chain, either linear, branched or cyclic) and mixtures thereof. The other metal source can alternatively be a tungsten or molybdenum source. The other metal source can be a titanium source such as $Ti(OR^1)_4$ or other alkoxide-containing metal sources, $M(NR^1R^2)_4$, or adducts containing these species. The second metal source can alternatively be a divalent metal source (preferably Sr, Ba, Mg, Ca, and Zn) selected from, but not limited to metal β-diketonates, cyclopentadienyl or adducts containing these species.

EXAMPLES

Synthesis of pentamethylcyclopentadienyl trimethoxy titanium $Ti(Me_5Cp)(OMe)_3$

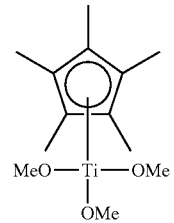

The synthesis is carried out. A yellow liquid is obtained. The purified compound is analyzed by NMR. A portion is analyzed by TGA. 50% of the mass is evaporated at 205° C. and the molecule is fully evaporated at 230° C., with a negligible amount of residues (cf FIG. 1). It shows the excellent stability of the molecule until the full evaporation temperature and the much higher volatility of this molecule compared to $Ti(OMe)_4$.

Synthesis of methylcyclopentadienyl trimethoxy titanium $Ti(MeCp)(OMe)_3$

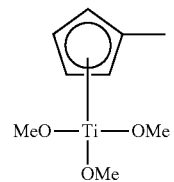

Figure 2:
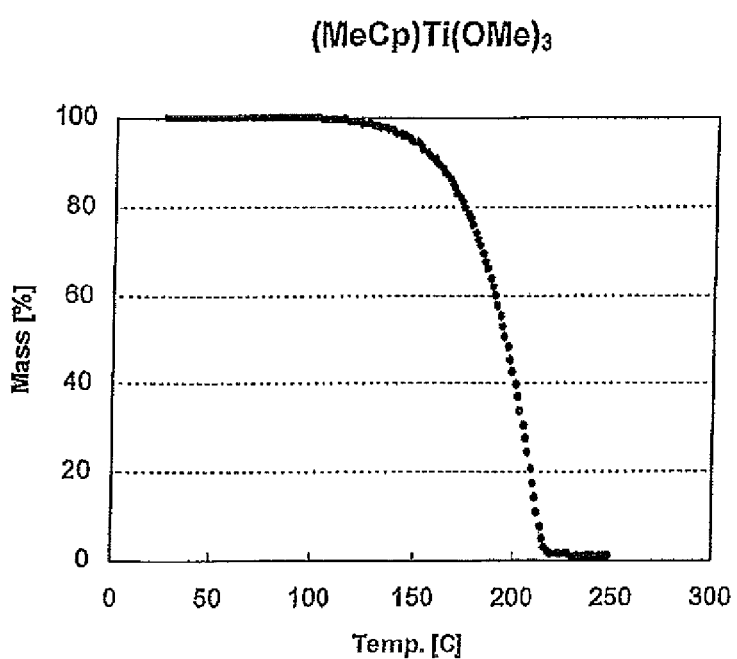
FIG. 2 is a graph of the percent residual mass of methylcyclopentadienyl trimethoxy titanium, $Ti(MeCp)(OMe)_3$, as a function of temperature during TGA.

The synthesis is carried out. A light yellow liquid is obtained. The purified compound is analyzed by NMR. A portion is analyzed by TGA. 50% of the mass is evaporated at 196° C. and the molecule is fully evaporated at 218° C., with a negligible amount of residues (cf FIG. 2). It shows the excellent stability of the molecule until the full evaporation temperature and the much higher volatility of this molecule compared to $Ti(OMe)_4$.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for forming a titanium-containing layer on a substrate, the method comprising at least the steps of:
   a) providing a vapor comprising a titanium precursor compound having the formula:
      Ti(Me$_5$Cp)(OR)$_3$, wherein Me=methyl, Cp=cyclopentadienyl, and each R is independently selected in the group consisting of methyl, ethyl, and isopropyl; and
   b) reacting the vapor with the substrate at a temperature of 380° C. to 600° C., according to an atomic layer deposition process, to form a layer of a titanium-containing complex on at least one surface of said substrate.

2. The method of claim 1, further comprising the step of:
   c) reacting the titanium-containing complex with a reagent selected from the group consisting of a metal source, reducing reactants, nitriding reactants, oxidizing reactants, and combinations thereof.

3. The method of claim 1, wherein the vapor further comprises a metal (M')-organic precursor and the titanium-containing complex further comprises a metal M'.

4. The method of claim 1, further comprising providing a reaction gas, wherein the reaction gas is selected from the group consisting of hydrogen, hydrogen sulfide, hydrogen selenide, hydrogen telluride, carbon monoxide, ammonia, organic amine, silane, disilane, higher silanes, silylamines, diborane, hydrazine, methylhydrazine, chlorosilane and chloropolysilane, metal alkyl, arsine, phosphine, trialkylboron, oxygen, ozone, water, hydrogen peroxide, nitrous oxide, nitrogen monoxide, nitrogen dioxide, alcohols, combinations thereof, combinations thereof, and radical species thereof.

5. The method of claim 4, wherein the reaction gas is ozone or water.

6. The method of claim 1, wherein an atomic layer deposition chamber containing the substrate has a pressure of 0.133 Pa to 133 kPa.

7. The method of claim 6, wherein the temperature is 380° C. to 425° C. and the pressure is below 27 kPa.

8. The method of claim 1, further comprising the step of purging excess vapor from the substrate with an inert gas selected from the group consisting of hydrogen, nitrogen, helium, argon, and mixtures thereof.

9. The method of claim 1, wherein the titanium-containing complex is formed on a semiconductor substrate.

10. The method of claim 1, wherein a titanium precursor compound is Ti(Me$_5$Cp)(OMe)$_3$.

11. The method of claim 5, wherein a titanium precursor compound is Ti(Me$_5$Cp)(OMe)$_3$.

12. The method of claim 11, wherein the reaction gas is ozone.

13. The method of claim 8, wherein a titanium precursor compound is Ti(Me$_5$Cp)(OMe)$_3$.

14. A method for forming a titanium-containing layer on a substrate, the method comprising at least the steps of:
   a) introducing into a reaction chamber a vapor comprising a titanium precursor compound having the formula:
      Ti(Me$_5$Cp)(OR)$_3$, wherein Me=methyl, Cp=cyclopentadienyl, and each R is independently selected in the group consisting of methyl, ethyl, and isopropyl;
   b) reacting the vapor with the substrate at a temperature of 380° C. to 600° C., according to an atomic layer deposition process;
   c) introducing into the reaction chamber a reagent selected from the group consisting of a metal source, reducing reactants, nitriding reactants, oxidizing reactants, and combinations thereof.

15. The method of claim 14, further comprising purging excess vapor from the substrate with an inert gas selected from the group consisting of hydrogen, nitrogen, helium, argon, and mixtures thereof*.

16. The method of claim 14, wherein steps a) through c) are repeated.

17. The method of claim 14, wherein the oxidizing reactant is ozone.

18. The method of claim 17, wherein the titanium precursor compound is Ti(Me$_5$Cp)(OMe)$_3$.

19. The method of claim 14, wherein the reagent is Sr(iPr$_3$Cp)$_2$, THF$_x$.

20. The method of claim 19, wherein the titanium precursor compound is Ti(Me$_5$Cp)(OMe)$_3$.

* * * * *